United States Patent [19]
Leeming et al.

[11] Patent Number: 6,059,980
[45] Date of Patent: May 9, 2000

[54] METHOD OF INHIBITING MICROBIAL GROWTH IN AN AQUEOUS MEDIUM

[75] Inventors: Karen Leeming, Bushey; Christopher P. Moore, Rayners Lane, both of United Kingdom

[73] Assignee: Eastman Kodak Company, Rochester, N.Y.

[21] Appl. No.: 09/112,628

[22] Filed: Jul. 9, 1998

[30] Foreign Application Priority Data

Aug. 2, 1997 [GB] United Kingdom .................. 9716350

[51] Int. Cl.[7] ....................................................... C02F 1/50

[52] U.S. Cl. ........................................... 210/755; 210/764

[58] Field of Search ................................... 210/764, 755; 162/161; 424/405

[56] References Cited

U.S. PATENT DOCUMENTS

| | | | |
|---|---|---|---|
| 4,067,997 | 1/1978 | Kabara | 424/312 |
| 4,105,431 | 8/1978 | Lewis et al. | 252/107 |
| 5,322,834 | 6/1994 | Hsu | 504/156 |
| 5,607,597 | 3/1997 | Wright et al. | 210/755 |

FOREIGN PATENT DOCUMENTS

| | | |
|---|---|---|
| 0 431 752A | 6/1991 | European Pat. Off. . |
| 0 733 304 | 9/1996 | European Pat. Off. . |

*Primary Examiner*—David A. Simmons
*Assistant Examiner*—Frank M. Lawrence

[57] ABSTRACT

A method of inhibiting microbial growth in an aqueous medium comprising contacting the aqueous medium with a biocidal material comprising a biocide having a log P value of at least 1.5 immobilized by hydrophobic exclusion on a support having a hydrophobic surface, characterized in that contact is made in the presence of a potentiating agent for the biocide.

10 Claims, 5 Drawing Sheets

METHOD OF INHIBITING MICROBIAL GROWTH IN AN AQUEOUS MEDIUM

FIELD OF THE INVENTION

The invention relates to a method of inhibiting microbial growth in an aqueous medium.

BACKGROUND OF THE INVENTION

Microbial growth occurs in many systems in which aqueous media such as water, aqueous solutions and aqueous dispersions are employed.

For example, significant biofouling can occur in many areas of photoprocessing systems and, in particular, where low flow rate washes and water recycling is used. The problem may be overcome by adding biocides to the wash water tanks when bacterial biofilm formation becomes evident visually. However at this point the biocides may not work and even at quite high concentrations are not particularly effective because the bacteria have attached to surfaces to form colonies which have built up in layers. Hence, any biocide in solution can only reach the outer biofilm layer and not the inner layers of the biofilm which are protected. Furthermore, widespread use of such biocides is not desirable because they are relatively expensive and toxic chemicals which require specialised disposal to protect the environment.

Potentiating agents are known to improve the performance of hydrophilic biocides in solution. They include compounds or a combination of compounds that can enhance synergistically the effect of a biocide without necessarily having an antimicrobial effect of their own.

For example, U.S. Pat. No. 5,322,834 describes synergistic biocidal compositions of certain water soluble isothiazolin-3-ones with one or more potentiating agents.

In contrast to the use of biocides in solution, EP-A-0 733 304 describes a biocidal material comprising a biocide immobilised on a support characterised in that the biocide has a log P value of at least 1.5, the support has a hydrophobic surface and the biocide is immobilised on the hydrophobic surface by hydrophobic exclusion. The support may take the form of polymer beads which may be held in a container having an inlet and an outlet so that the aqueous medium to be treated can be contacted with the beads by passing it through the container. An advantage of the material is that the hydrophobic biocide remains attached to the support during use i.e. there is no free biocide in solution. The material may be used to inhibit microbial growth in the wash water or other solutions used in a photoprocessor.

The immobilised hydrophobic biocides are believed to reach their site of action in a different way to the hydrophilic biocides. It is clear that hydrophobic biocides must operate by a different mechanism to hydrophilic biocides because of their different characters. The use of potentiating agents in combination with hydrophobic biocides is unknown and there is no reason to suppose that potentiating agents for the known water soluble biocides would be effective in combination with the immobilised biocides.

PROBLEM TO BE SOLVED BY THE INVENTION

There is a need to improve the efficiency of control of the growth of microorganisms using the immobilised biocide described above.

SUMMARY OF THE INVENTION

The invention provides a method of inhibiting microbial growth in an aqueous medium comprising contacting the aqueous medium with a biocidal material comprising a biocide having a log P value of at least 1.5 immobilised by hydrophobic exclusion on a support having a hydrophobic surface, characterised in that contact is made in the presence of a potentiating agent for the biocide.

ADVANTAGEOUS EFFECT OF THE INVENTION

The invention permits more efficient control of the growth of microorganisms. It facilitates the use of less biocide and does not require the addition of conventional biocides to the solution, thus making it a more environmentally acceptable approach to the control of biogrowth in, for example, photoprocessor wash waters.

DETAILED DESCRIPTION OF THE INVENTION

It has been found unexpectedly that potentiating agents can be used successfully with hydrophobic biocides immobilised on a support by a hydrophobic exclusion mechanism.

Biocides for use in the invention have a log P value of at least 1.5 wherein P represents the partition coefficient between n-octanol and water defined as follows $$P = \frac{[\text{biocide}]_{octanol}}{[\text{biocide}]_{water}}$$

Log P is a well known term used in literature on biocides. As used herein, it provides a measure of the hydrophobicity of the biocide.

Biocides which may be employed include any known biocide meeting the hydrophobicity requirement or a known biocide which has been hydrophobically modified to meet the requirement.

Suitable types of biocide include those described in "*Microbiocides for the Protection of Materials*", W. Paulus, published by Chapman Hall, 1993. They are agents capable of killing or inhibiting the multiplication of microorganisms such as bacteria, yeasts, fungi, algae and lichens. Examples include heterocyclic N,S compounds, compounds with activated halogen groups and quaternary ammonium salts.

Preferred biocides include those currently employed in the treatment of photoprocessing systems e.g. isothiazolinones.

Examples of isothiazolinone biocides are those having the structure wherein
R represents hydrogen, alkyl, aryl, alkaryl and aralkyl; and, $R^1$ and $R^2$ independently represent hydrogen, halogen, alkyl, or $R^1$ and $R^2$ taken together represent the atoms necessary to complete a fused carbocyclic ring, preferably a 5- or 6-membered ring e.g. a benzene ring; provided that R, $R^1$ and $R^2$ are chosen so that the log P value of the compound is at least 1.5.

Preferred biocides include those having the following structures:

wherein $R^3$ is an alkyl group having from 4 to 20 carbon atoms or an aryl group having from 6 to 20 carbon atoms;

wherein $R^5$ and $R^6$ are selected from hydrogen and halogen, and $R^4$ is an alkyl group having from 5 to 20 carbon atoms; and, wherein each of $R^7$, $R^8$ and $R^9$ is hydrogen or an alkyl group providing a total of from 2 to 20 carbon atoms; $R^{10}$ is substituted or unsubstituted alkyl or aryl e.g. phenoxyethyl; and, Y is any suitable counter anion e.g. halide.

Specific examples of commercially available isothiazolinone biocides include

Proxel™ (manufactured by Zeneca):

Promexal™ (manufactured by Zeneca):

Kathon™ (manufactured by Rohm and Haas):

X = H, Cl

Other commercially available biocides are:
Bronopol™ (manufactured by Boots):

Domiphen™ bromide (manufactured by Ciba-Geigy):

Vantocil™ (manufactured by Zeneca):

(n = 12)

Densil S™ (manufactured by Zeneca):

Biocides which are hydrophobically modified Proxel™ and Kathon™ have been prepared having the following structures:

$R^4$=—$(CH_2)_7CH_3$ , $R^5$=H, $R^6$ =Cl (Compound 3)
$R^4$=—$(CH_2)_{17}CH_3$ , $R^5$=H, $R^6$ =Cl (Compound 4)
$R^4$=—$(CH_2)_7CH_3$ , $R^5$=H, $R^6$ =H (Compound 5)

$R^4$=—$(CH_2)_7CH_3$, $R^5$=Cl, $R^6$=Cl (Compound 6)

Many commercially available biocides are soluble in aqueous media and an increase in their hydrophobicity is required to render them suitable for use in the invention.

It is essential that biocides having a log P of at least 1.5 are used in the invention. Biocides having a log P less than 1.5 can become detached from the support and contaminate the aqueous medium.

Hydrophobic polymers suitable for use as support materials include any inert, water insoluble polymers.

Examples of suitable polymers are ethenic polymers including polyolefins, polystyrene, polyvinyl chloride, polyvinyl acetate and acrylic polymers; and polymers formed by condensation reactions including polyesters, polyamides, polyurethanes, polyethers, epoxy resins, amino resins and phenol-aldehyde resins.

Specific examples of support materials are Amberlite™ XAD-4 and XAD-2 resin beads which are both highly porous, cross-linked polystyrene.

The support may take a variety of forms e.g. particulate, sheet or fibre. It may be porous or non-porous.

The biocide is immobilised on the support by a hydrophobic exclusion mechanism. Immobilisation may be carried out by addition of the dry support e.g. a resin to a solution of the biocide in an organic solvent e.g. tetrahydrofuran (THF), followed by slow addition of a similar volume of water. As the volume fraction of water increases, the biocide and the support associate to exclude water by the well known hydrophobic effect. The support may be left in contact with the solution for a period of time e.g. 18 hours allowing most of the organic solvent to evaporate. Subsequent drying of the support leaves the biocide adsorbed thereto.

Alternatively, immobilisation may be carried out by adding water to the dry support, contacting the support with a solution of the biocide in an organic solvent e.g. heptane, and removing the solvent e.g. by evaporation under reduced pressure.

The hydrophobic exclusion mechanism by which the biocide is immobilised is a reversible physisorption wherein the biocide is hydrophobically bound to the support.

A variety of commercial and hydrophobically-modified biocides have been studied. Partition coefficients between octanol and water have been determined at 25° C. by UV/visible absorption. First, the calibration curve of each biocide was determined as optical density ($OD_{abs}$) versus concentration of biocide in µg/g (ppm) of water for the predominantly water-soluble materials and µg/g of octanol for the predominantly oil-soluble biocides.

A known amount of biocide was placed in a glass vessel containing either 10 ml of water or 10 ml of octanol depending on the solubility of the biocide. An equal volume of the other solvent was added and the glass vessel sealed. The vessel was shaken vigorously for a few minutes and then every few hours for more than 48 hours. Each mixture was placed in a sealed separating funnel and left for a further 24 hours. The water phase of each mixture was removed and the UV/visible spectra run against water with appropriate dilutions to bring absorbance between 0 and 1.5 for the commercial biocides and the octanol fractions were examined for the hydrophobically modified biocides.

The following partition coefficients shown in Table 1 were determined.

TABLE 1

| Biocide | P |
|---------|---|
| Promexal ™ | ~4.5 |
| Vantocil ™ | ~0.3 |
| Domiphen ™ | ~50 |
| Kathon ™ | ~1 |
| Proxel ™ | ~0* |
| Compound 1 | >330 |
| Compound 3 | >560 |
| Compound 2 | >130 |
| Compound 4 | >480 |

*i.e. there was almost no biocide in the oil phase.

The log P value of the biocides which are used in the invention must be at least 1.5, preferably at least 2.0.

Potentiating agents include compounds or a combination of compounds that can enhance synergistically the effect of the immobilised biocide without necessarily having an antimicrobial effect of their own.

Representative potentiating agents may be selected from chelating agents e.g. alkylenediaminetetraacetic acids such as EDTA (ethylenediaminetetraacetic acid), anionic surfactants e.g. alkylarylpolyalkoxy sulphonates such as TX200 (an alkylarylpolyethoxy sulphonate) available from Rohm & Haas, and biocides e.g. 1,3,5-substituted-hexahydro-s-triazines such as Acticide™ GR (hexahydro-1,3,5-tris(2-hydroxyethyl)-s-triazine) available from Thor Chemicals and 2-substituted-1, 3-propanediols such as Bronopol™ (2-bromo-2-nitro-1, 3-propanediol) available from Boots.

The potentiating agent may be used in an amount from 1 ppm to 5000 ppm, preferably from 10 ppm to 1000 ppm, more preferably from 10 ppm to 500 ppm.

In use, the aqueous medium is brought into contact with the biocidal material. Different ways of achieving contact include passing the aqueous medium through a container e.g. a column containing the material in particulate form, passing the aqueous medium through a filter of the material and passing the aqueous medium over the material in the form of a surface coating.

The biocidal material is of particular use in photoprocessing systems. Such systems comprise stages for developing, fixing, bleaching and washing an exposed photographic material. Each stage requires apparatus for applying the appropriate aqueous processing solution to the photographic material. The apparatus may comprise means for supplying, removing and, possibly, recirculating such solutions.

The biocidal material may be used to inhibit microbial growth in the wash water or other solutions used in a photoprocessor.

Figure 1:
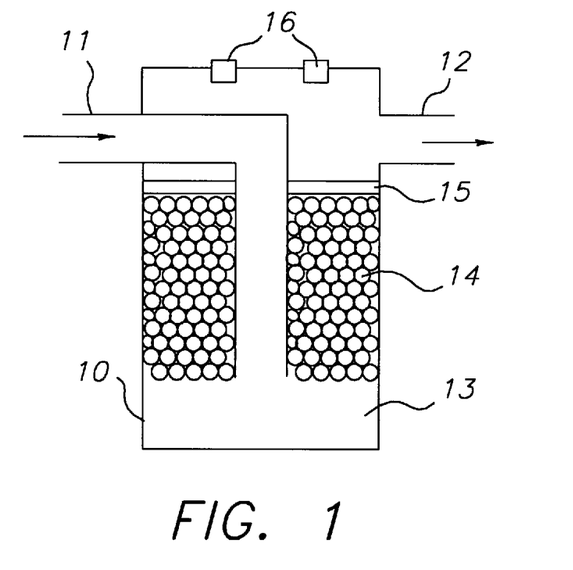
FIG. 1 is a schematic representation of a device holding biocidal material.

FIG. 1 is a schematic representation of apparatus for use in performing the method of the invention. The apparatus comprises a container 10 having fluid inlet means 11 and fluid outlet means 12 said inlet and outlet means 11, 12 communicating with an inner chamber 13 of the container. When the apparatus is in use, fluid entering the inner chamber through the inlet means 11 flows through the chamber 13 and leaves the container through the outlet means 12. The inner chamber 13 holds a biocidal material in accordance with the invention in the form of particles 14. A filter 15 to retain the particles is positioned at the top of the inner chamber to prevent loss of the particles from the device. The top of the container 10 is provided with plugs 16 (optional) for venting any gas which accumulates in the device.

Fluid entering the device flows down a central tube and subsequently flows up through the particles. The arrows indicate the direction of the flow of fluid through the device.

Figure 2:
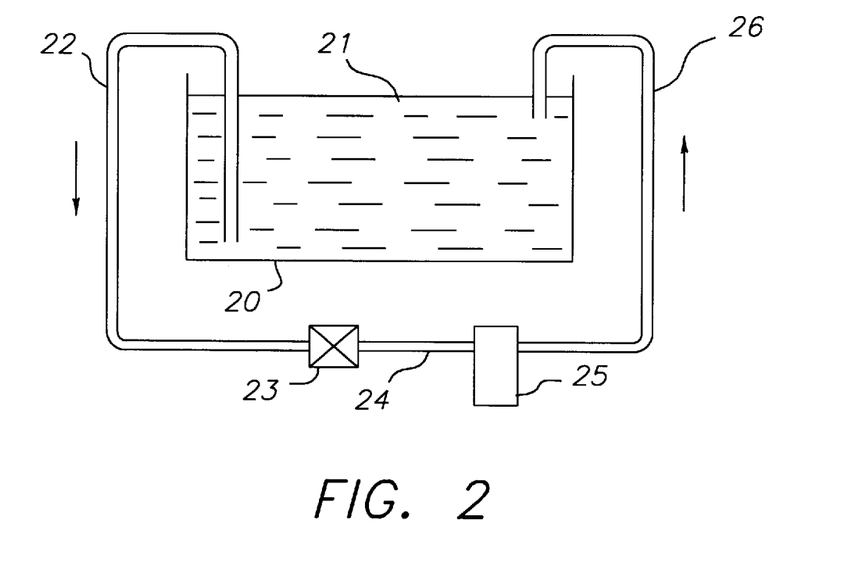
FIG. 2 is a schematic representation of the use of the device shown in FIG. 1.
Figure 3:
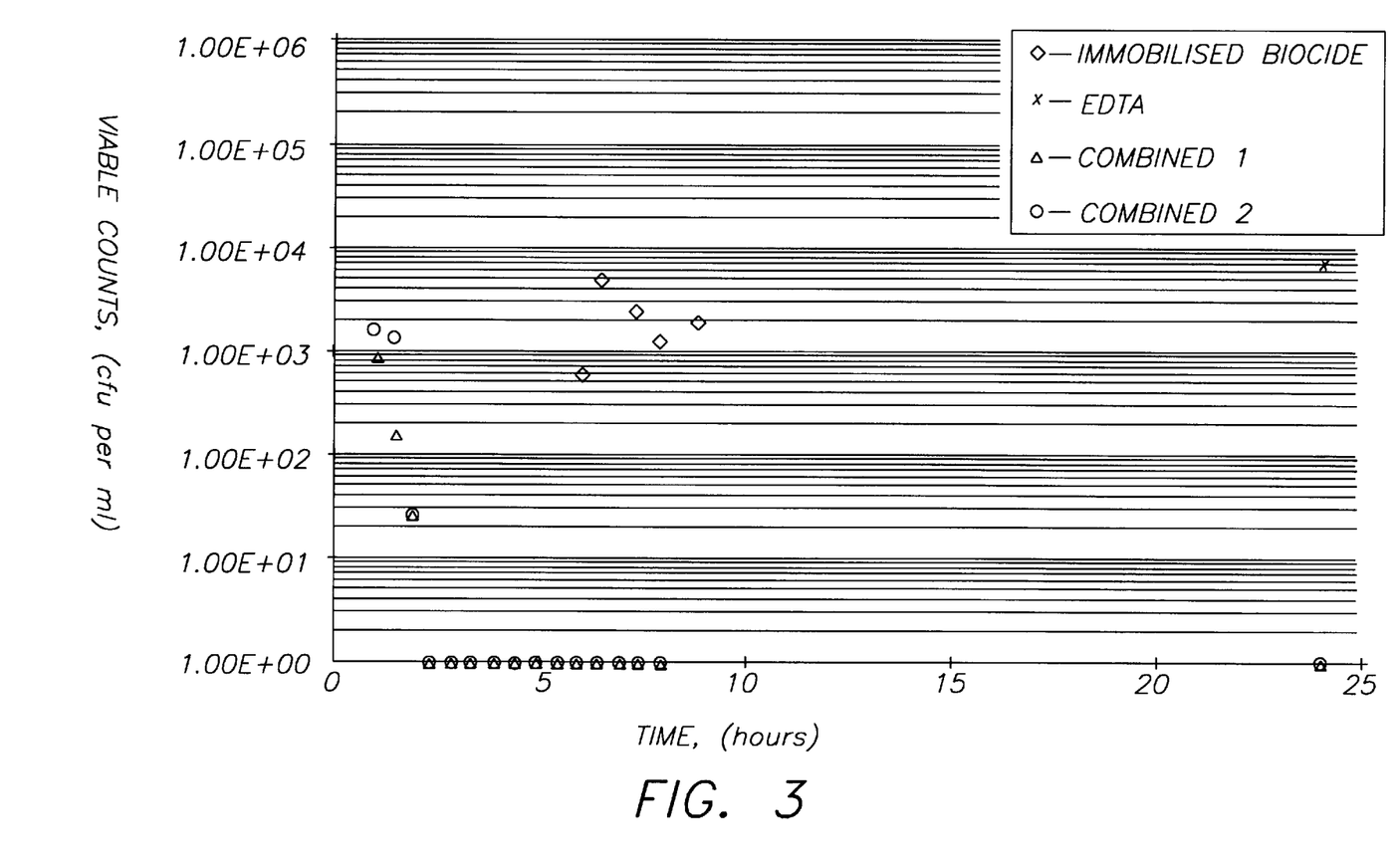
FIGS. 3 to 6 are each a graphical representation of results achieved using the method of the invention in accordance with the Example described hereinafter.
Figure 4:
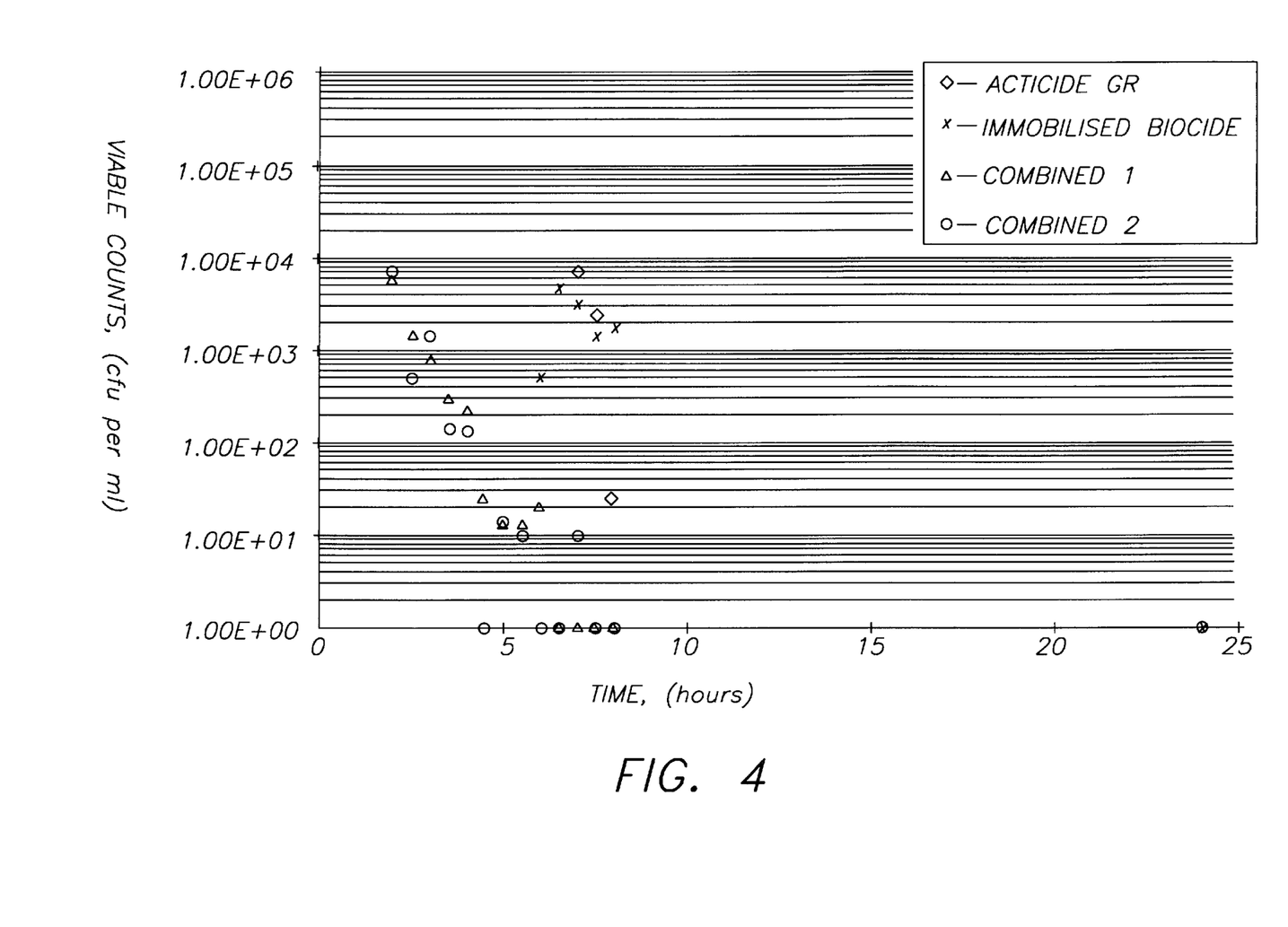
Figure 5:
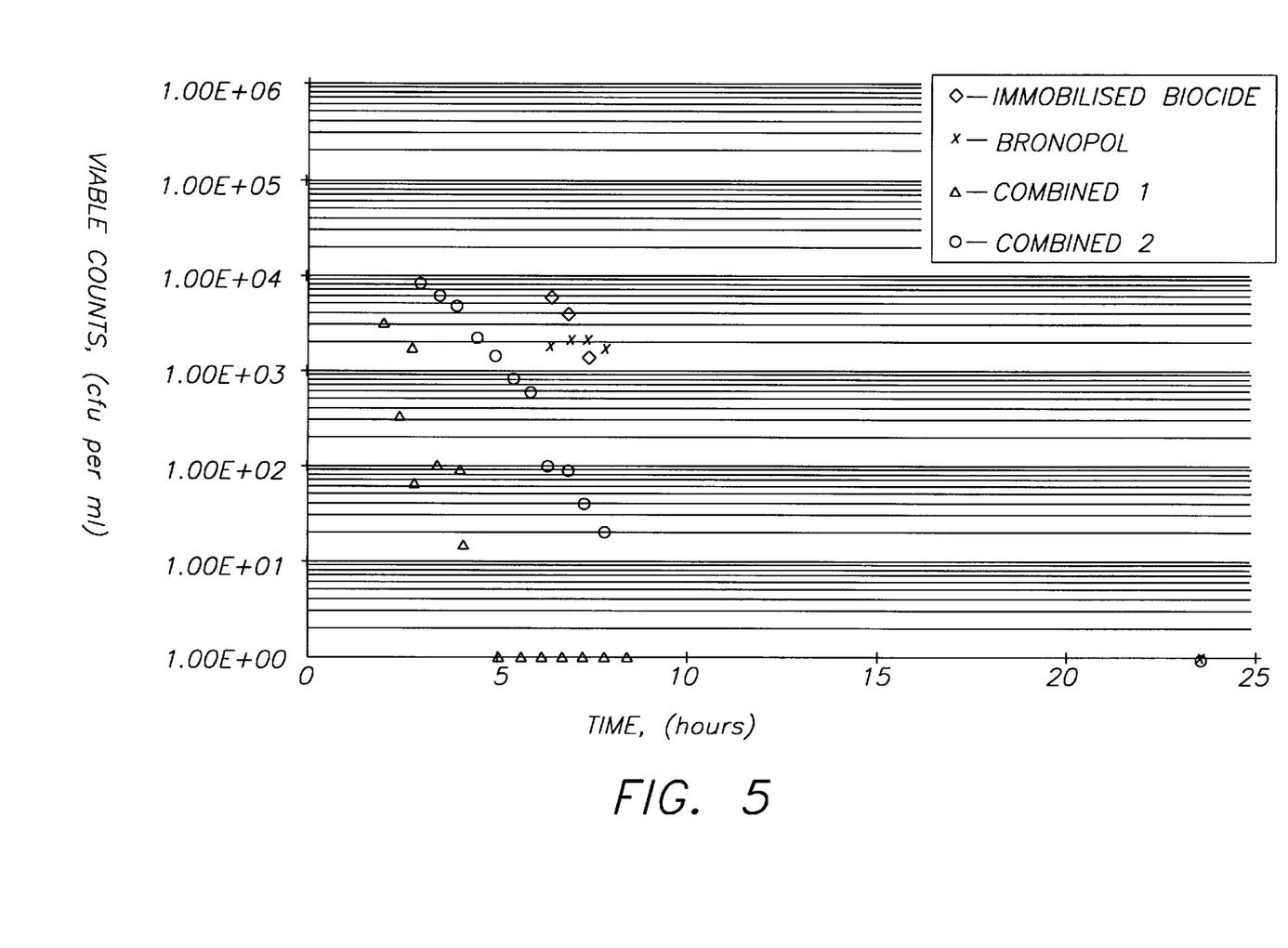
Figure 6:
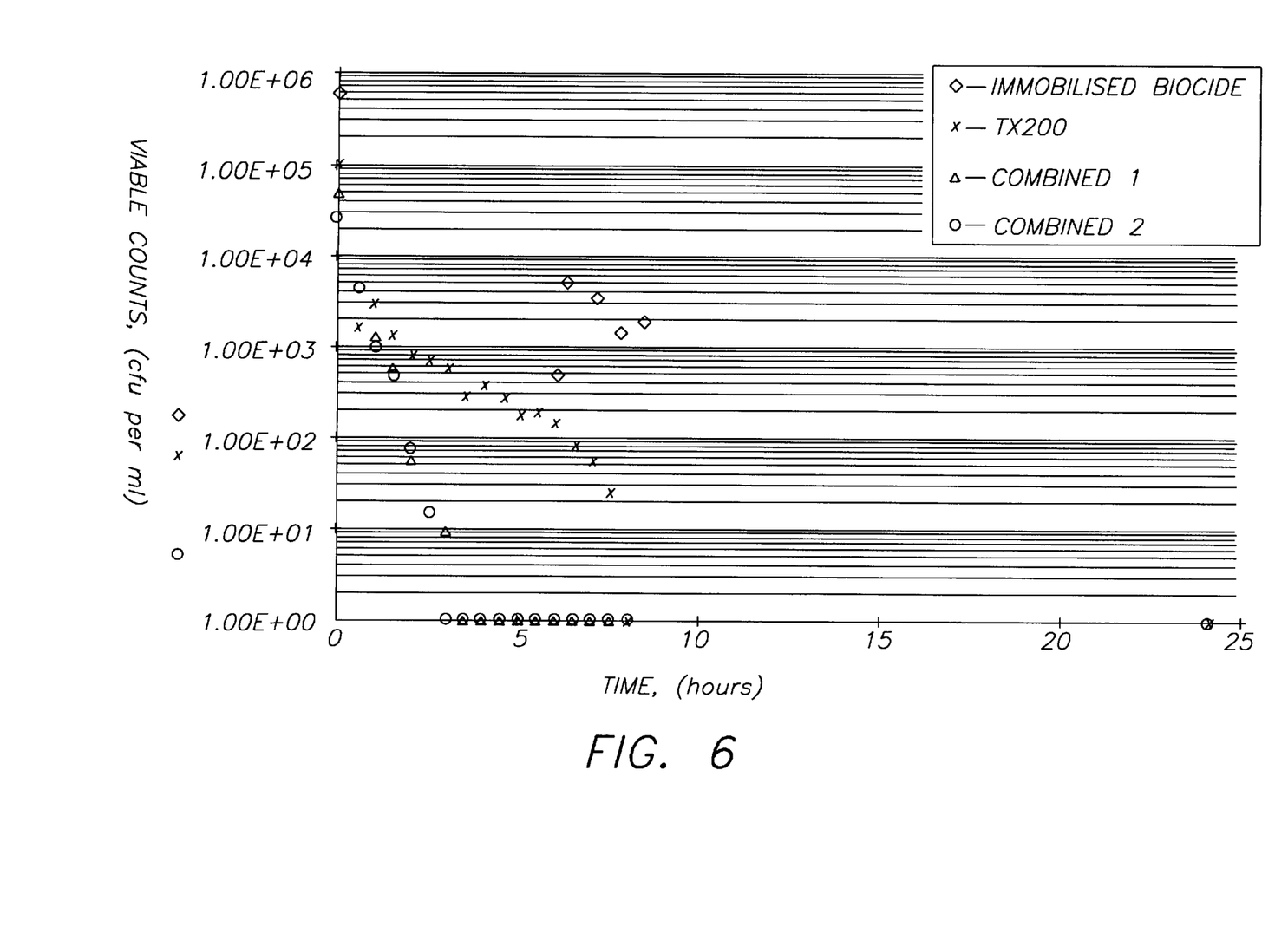

FIG. 2 is a schematic representation of the use of the apparatus shown in FIG. 1. A tank 20 containing water 21 is shown e.g. the wash water tank of a photoprocessor. Tubing 22 has an open end in the water 21 at the bottom of tank 20, the other end being connected to the inlet of a pump 23 outside the tank 20. Tubing 24 connects the outlet of the pump 23 to the inlet of a device 25 of the type shown in FIG. 1. One end of tubing 26 is connected to the outlet of device 25 and the other end opens into the top of tank 20.

In use, water is pumped from the bottom of tank 20 through device 25 and back into tank 20 in a recirculation loop. The arrows indicate the direction of the flow of water around the loop.

The invention is further illustrated by way of example as follows.

EXAMPLE

This example demonstrates the use of EDTA, Acticide™ GR, Bronopol™ and TX200 as potentiating agents with the biocide Kathon™ 287T (Compound 6) immobilised on Amberlite™ XAD-7HP polyacrylate resin beads (approximately 20% w/w).

The immobilised biocide was prepared in accordance with the following procedure. A sample of Kathon™ 287T biocide (8.0 g) was melted on a steam bath and weighed into a preweighed round bottomed flask. Heptane (68 ml) was warmed on a steam bath, added to the biocide and stirred with a magnetic stirrer bar until all the biocide had dissolved. Pre-dried Amberlite™ XAD-7 resin beads (24.0 g) were weighed into a beaker. Water (16 ml) was added and the mixture stirred until all the water had been incorporated into the beads. The beads were added to the heptane solution and stirred for 15 minutes. The liquid was evaporated under reduced pressure on a rotary evaporator until the beads became free flowing.

The individual potentiating agents and immobilised biocide were tested in an aqueous system containing approximately $10^5$ bacteria per ml (*Pseudomonas aeruginosa*). The potentiating agents were evaluated individually by adding a known level of the agent to 10 ml of sterile water. An inoculum of pre-prepared bacterial culture was added to each flask. A time zero, a small aliquot of the bacterial culture was removed from each flask to perform initial viable counts. Viable counts were then performed at half hourly intervals until 8 hours and then again at 24 hours by removing a small aliquot from each flask and performing a serial dilution series and plating onto nutrient agar plates. The data is summarised in FIGS. 3–6.

The immobilised biocide was evaluated by placing 1 g of resin beads in a 25 ml conical flask and sterilising by autoclaving at 120° C. for more than 20 minutes. 10 ml of sterile water was added to the flask and an inoculum of pre-prepared bacterial culture was added to the flask to give approximately $10^5$ to $10^6$ bacteria per ml. At time zero, a small aliquot was removed from the flask to perform initial viable counts. Viable counts were then performed at half hourly interval until 8 hours and then again at 24 hours by removing a small aliquot from the flask and performing a serial dilution series and plating onto nutrient agar plates. The data is summarised in FIGS. 3–6.

The individual potentiating agents were then evaluated with the immobilised biocide in the same way, with 1 g of resin beads in 10 ml of sterile water containing the potentiating agent. Two evaluations were made for each immobilised biocide.

The results obtained in respect of each potentiating agent are tabulated in Tables 1 to 4 below. The same results are plotted in FIGS. 3 to 6.

TABLE 1

| TIME, hours | Immobilised biocide | EDTA 465 ppm | Combined 1 | Combined 2 |
| --- | --- | --- | --- | --- |
| 0 | 5.73E + 05 | 4.85E + 05 | 2.13E + 05 | 2.37E + 05 |
| 0.5 | | | | |
| 1 | | | 8.20E + 02 | 1.60E + 03 |
| 1.5 | | | 1.60E + 02 | 1.35E + 03 |
| 2 | | | 25 | 25 |
| 2.5 | | | 1 | 1 |
| 3 | | | 1 | 1 |
| 3.5 | | | 1 | 1 |
| 4 | | | 1 | 1 |
| 4.5 | | | 1 | 1 |
| 5 | | | 1 | 1 |
| 5.5 | | | 1 | 1 |
| 6 | 5.70E + 02 | | 1 | 1 |
| 6.5 | 5.25E + 03 | | 1 | 1 |
| 7 | 3.40E + 03 | | 1 | 1 |
| 7.5 | 1.56E + 03 | | 1 | 1 |
| 8 | 1.92E + 03 | | 1 | 1 |
| 24 | 1 | 7.59E + 03 | 1 | 1 |

TABLE 2

| TIME, hours | Immobilised biocide | Acticide GR 150 ppm | Combined 1 | Combined 2 |
| --- | --- | --- | --- | --- |
| 0 | 5.73E + 05 | 2.16E + 05 | 1.77E + 05 | 2.76E + 05 |
| 0.5 | | | | |
| 1 | | | | |
| 1.5 | | | | |
| 1.97 | | | 6.07E + 03 | 7.66E + 03 |
| 2.5 | | | 1.60E + 03 | 5.20E + 02 |
| 3 | | | 8.60E + 02 | 1.53E + 03 |
| 3.5 | | | 3.05E + 02 | 1.50E + 02 |
| 4 | | | 2.15E + 02 | 1.45E + 02 |
| 4.5 | | | 25 | 1 |
| 5 | | | 15 | 15 |
| 5.5 | | | 15 | 10 |
| 6 | 5.70E + 02 | | 20 | 1 |
| 6.5 | 5.25E + 03 | 5.74E + 03 | 1 | 1 |
| 7 | 3.40E + 03 | 6.90E + 03 | 1 | 10 |
| 7.5 | 1.56E + 03 | 2.54E + 03 | 1 | 1 |
| 8 | 1.92E + 03 | 25 | 1 | 1 |
| 24 | 1 | 1 | 1 | 1 |

TABLE 3

| TIME, hours | Immobilised biocide | Bronopol 12.55 ppm | Combined 1 | Combined 2 |
| --- | --- | --- | --- | --- |
| 0 | 5.73E + 05 | 4.76E + 05 | 3.91E + 05 | 4.50E + 05 |
| 0.5 | | | | |
| 1 | | | | |
| 1.5 | | | 4.20E + 03 | |
| 2 | | | 2.60E + 03 | |
| 2.5 | | | 3.35E + 02 | |
| 3 | | | 65 | 8.30E + 03 |
| 3.5 | | | 1.00E + 02 | 6.26E + 03 |
| 4 | | | 90 | 4.98E + 03 |
| 4.5 | | | 15 | 2.25E + 03 |
| 5 | | | 1 | 1.50E + 03 |
| 5.5 | | | 1 | 8.20E + 02 |
| 6 | 5.70E + 02 | | 1 | 5.80E + 02 |
| 6.5 | 5.25E + 03 | 1.86E + 03 | 1 | 95 |
| 7 | 3.40E + 03 | 2.17E + 03 | 1 | 90 |
| 7.5 | 1.56E + 03 | 2.14E + 03 | 1 | 40 |
| 8 | 1.92E + 03 | 1.82E + 03 | 1 | 20 |
| 24 | 1 | 1 | 1 | 1 |

TABLE 4

| TIME, hours | Immobilised biocide | TX200 1.375 ppm | Combined 1 | Combined 2 |
| --- | --- | --- | --- | --- |
| 0 | 5.73E + 05 | 9.90E + 04 | 3.70E + 04 | 2.45E + 04 |
| 0.5 | | 1.68E + 03 | | 4.41E + 03 |
| 1 | | 2.97E + 03 | 1.40E + 03 | 1.04E + 03 |
| 1.5 | | 1.44E + 03 | 5.50E + 02 | 4.75E + 02 |
| 2 | | 7.75E + 02 | 50 | 75 |
| 2.5 | | 7.25E + 02 | 15 | 15 |
| 3 | | 6.15E + 02 | 10 | 1 |
| 3.5 | | 2.95E + 02 | 1 | 1 |
| 4 | | 3.90E + 02 | 1 | 1 |
| 4.5 | | 2.80E + 02 | 1 | 1 |
| 5 | | 1.80E + 02 | 1 | 1 |
| 5.5 | | 1.90E + 02 | 1 | 1 |
| 6 | 5.70E + 02 | 1.50E + 02 | 1 | 1 |
| 6.5 | 5.25E + 03 | 85 | 1 | 1 |
| 7 | 3.40E + 03 | 55 | 1 | 1 |
| 7.5 | 1.56E + 03 | 25 | 1 | 1 |
| 8 | 1.92E + 03 | 1 | 1 | 1 |
| 24 | 1 | 1 | 1 | 1 |

The results demonstrate that the speed at which the control of microbial growth could be achieved was improved relative to the control where no potentiating agent was used. Since the immobilised biocide is known to be supplied to the microorganism on demand and not released to solution, the potentiating agent is acting synergistically.

We claim:

1. A method of inhibiting microbial growth in an aqueous medium comprising contacting the aqueous medium with a biocidal material comprising a biocide having a log P value of at least 1.5 immobilised by hydrophobic exclusion on a support having a hydrophobic surface, characterised in that contact is made in the presence of a potentiating agent for the biocide.

2. A method according to claim 1 wherein wherein the biocide has the structure wherein R represents hydrogen, alkyl, aryl, alkaryl and aralkyl; and, $R^1$ and $R^2$ independently represent hydrogen, halogen, alkyl, or $R^1$ and $R^2$ taken together represent the atoms necessary to complete a fused carbocyclic ring.

3. A method according to claim 1 wherein the biocide has the structure wherein $R^4$ is an alkyl group having from 5 to 20 carbon atoms; and, $R^5$ and $R^6$ are selected from hydrogen and halogen.

4. A method according to claim 3 wherein $R^4$=—$(CH_2)_7CH_3$, $R^5$ =Cl, and $R^6$=Cl.

5. A method according to claim 1 wherein the potentiating agent is selected from alkylenediaminetetraacetic acids, alkylarylpolyalkoxy sulphonates, 1,3,5-substituted-hexahydro-s-triazines and 2-substituted-1,3-propanediols.

6. A method according to claim 5 wherein the potentiating agent is selected from ethylenediaminetetraacetic acid, alkylarylpolyethoxy sulphonates, hexahydro-1,3,5-tris (2-hydroxyethyl)-s-triazine and 2-bromo-2-nitro-1,3-propanediol.

7. A method according to claim 5 wherein the potentiating agent is used in an amount from 1 ppm to 5000 ppm.

8. A method according to claim 5 wherein the support is a hydrophobic polymer.

9. A method according to claim 8 wherein the support is in the form of polymer beads.

10. A method according to claim 8 wherein the support is porous.

* * * * *